United States Patent
Wang

(10) Patent No.: US 8,709,056 B2
(45) Date of Patent: Apr. 29, 2014

(54) PHOTOTHERAPY APPARATUS WITH BUILT-IN ULTRASONIC IMAGE MODULE

(75) Inventor: Sean Xiaolu Wang, Wilmington, DE (US)

(73) Assignee: BWT Property Inc, Newark, DE (US)

( * ) Notice: Subject to any disclaimer, the term of this patent is extended or adjusted under 35 U.S.C. 154(b) by 1223 days.

(21) Appl. No.: 11/697,770

(22) Filed: Apr. 9, 2007

(65) Prior Publication Data

US 2007/0239146 A1 Oct. 11, 2007

Related U.S. Application Data

(60) Provisional application No. 60/767,488, filed on Apr. 10, 2006.

(51) Int. Cl.
*A61N 5/06* (2006.01)
*A61B 8/00* (2006.01)

(52) U.S. Cl.
USPC ............... 607/88; 607/90; 600/439; 128/898

(58) Field of Classification Search
USPC ............. 607/88–92; 606/9–12; 600/437–439, 600/442–447; 128/898
See application file for complete search history.

(56) References Cited

U.S. PATENT DOCUMENTS

| | | | |
|---|---|---|---|
| 3,866,032 A | 2/1975 | Veres | |
| 4,034,480 A | 7/1977 | Mehrtens | |
| 4,064,424 A | 12/1977 | Hergenrother | |
| 4,183,078 A | 1/1980 | Kidd | |
| 4,430,695 A | 2/1984 | Payne et al. | |
| 4,532,512 A | 7/1985 | Tanner | |
| 4,887,605 A * | 12/1989 | Angelsen et al. | 600/439 |
| 5,139,334 A | 8/1992 | Clarke et al. | |
| 5,224,773 A | 7/1993 | Arimura | |
| 5,287,104 A | 2/1994 | Shemwell | |
| 5,377,683 A | 1/1995 | Barken | |
| 5,608,290 A | 3/1997 | Hutchisson | |
| 5,655,308 A | 8/1997 | McDermott | |
| 5,804,829 A | 9/1998 | Palmer | |
| 5,967,984 A | 10/1999 | Chu et al. | |
| 5,982,484 A | 11/1999 | Clarke et al. | |
| 6,007,219 A | 12/1999 | O'Meara | |
| 6,030,099 A | 2/2000 | McDermott | |
| 6,048,083 A | 4/2000 | McDermott | |
| 6,086,220 A | 7/2000 | Lash et al. | |
| 6,100,975 A | 8/2000 | Smith et al. | |
| 6,135,994 A | 10/2000 | Chernoff | |
| 6,168,294 B1 | 1/2001 | Erni et al. | |
| 6,200,310 B1 * | 3/2001 | Ben-Haim et al. | 606/10 |
| 6,210,425 B1 * | 4/2001 | Chen | 607/88 |
| 6,224,216 B1 | 5/2001 | Parker et al. | |
| 6,238,426 B1 * | 5/2001 | Chen | 607/88 |
| 6,299,622 B1 * | 10/2001 | Snow et al. | 606/159 |
| 6,354,714 B1 | 3/2002 | Rhodes | |
| 6,446,467 B1 | 9/2002 | Lieberman et al. | |

(Continued)

*Primary Examiner* — Ahmed Farah
(74) *Attorney, Agent, or Firm* — Frank F. Tian

(57) ABSTRACT

This invention discloses a phototherapy apparatus for biological tissue (preferably skin tissue) treatment. The phototherapy apparatus comprises one or more light sources and a built-in ultrasonic imaging module. The ultrasonic imaging module provides a high-resolution image of the biological tissue from its surface layer to a depth of a few centimeters. The image is utilized to optimize the phototherapy procedure in parameters such as light intensity, wavelength, spot size, divergence angle, duration, repetition rate, duty cycle, etc. and to evaluate the effectiveness of the phototherapy procedure.

3 Claims, 2 Drawing Sheets

(56) References Cited

U.S. PATENT DOCUMENTS

| | | |
|---|---|---|
| 6,464,373 B1 | 10/2002 | Petrick |
| 6,489,733 B1 | 12/2002 | Schmidt et al. |
| 6,543,911 B1 | 4/2003 | Rizkin et al. |
| 6,563,854 B2 | 5/2003 | Tedesco et al. |
| 6,688,755 B2 | 2/2004 | O'Meara |
| 6,753,762 B1 | 6/2004 | Jorba Gonzalez |
| 6,761,729 B2 * | 7/2004 | Babaev ............ 607/89 |
| 6,902,291 B2 | 6/2005 | Rizkin et al. |
| 6,905,228 B1 | 6/2005 | Takeyasu et al. |
| 6,932,496 B2 | 8/2005 | Rizkin et al. |
| 6,947,571 B1 | 9/2005 | Rhoads et al. |
| 7,021,801 B2 | 4/2006 | Mohacsi |
| 7,217,266 B2 * | 5/2007 | Anderson et al. ............ 606/12 |
| 7,615,008 B2 * | 11/2009 | Zhang et al. ............ 600/437 |
| 2003/0136837 A1 | 7/2003 | Amon |
| 2003/0187742 A1 | 10/2003 | Yamagishi |
| 2004/0095777 A1 | 5/2004 | Trenchard et al. |
| 2005/0110649 A1 | 5/2005 | Fredericks et al. |
| 2005/0111723 A1 | 5/2005 | Hannigan et al. |
| 2006/0082760 A1 | 4/2006 | Lin |
| 2006/0250801 A1 | 11/2006 | Trenchard et al. |

* cited by examiner

PHOTOTHERAPY APPARATUS WITH BUILT-IN ULTRASONIC IMAGE MODULE

REFERENCE TO RELATED APPLICATIONS

This application claims an invention which was disclosed in Provisional Patent Application No. 60/767,488, filed Apr. 10, 2006, entitled "Phototherapy Apparatus with Built-in Ultrasonic Imaging Module". The benefit under 35 USC §119 (e) of the above mentioned United States Provisional Applications is hereby claimed, and the aforementioned application is hereby incorporated herein by reference.

FIELD OF THE INVENTION

This invention generally relates to a phototherapy apparatus, and more specifically to a phototherapy apparatus with a built-in ultrasonic imaging module.

BACKGROUND

Phototherapy relates to treatment of biological tissues, preferably skin tissues, using visible, ultraviolet, and/or infrared lights. The light treatment may be applied solely for sterilization, bio-modulation, and photo-rejuvenation. Alternatively, the treatment may be used in combination with certain photo-sensitive drugs or nutrition supplements. In comparison with laser surgery, the light intensity employed in phototherapy is much lower. Thus the light sources used in phototherapy are not limited to lasers but may include light emitting diodes (LEDs) and/or certain lamps as well. Typical applications of phototherapy include wound healing, pressure ulcer treatment, psoriasis reduction, skin rejuvenation, etc.

Certain abnormal skin conditions, such as pressure ulcer, develop from the subcutaneous tissue and are hardly observable from the surface layer of the skin in their early stages. This places a barrier for using phototherapy to treat these abnormal skin conditions when they are still in their early phases, when the phototherapy is most effective. In addition, phototherapy generally causes only subtle changes to the surface layer of the tissue and in some cases its impact only occurs in the inner layer of the tissue. This makes it difficult to evaluate the effectiveness of the phototherapy procedure. Therefore, it is desirous to overcome the above barriers with improved devices.

Ultrasonic imaging techniques are known to be employed in laser surgery apparatus.

In U.S. Pat. No. 5,377,683 to Barken, a catheter having an ultrasound transducer and a plurality of optical fibers for conveying laser light from an external laser source to the tip of the catheter is described. The ultrasound and the laser are connected to a computer system which is used to display ultrasonic images of internal tissue areas within the patient's body and control firing of the laser in response to delimiting input from the physician.

In U.S. Pat. No. 5,967,984 to Chu et al., a catheter having a catheter body of extended length for insertion within a body of a living being is described. The catheter includes an ultrasound imaging device disposed within a distal portion of the catheter body to display a real-time image of tissue surrounding the distal portion of the catheter. The catheter further includes a cutting element, e.g., an electrode wire or a laser fiber. The ultrasound imaging device is positioned relative to the cutting element such that the real-time image produced by the ultrasound imaging system can include the cutting element in relation to the tissue.

In U.S. Pat. No. 6,135,994 to Chernoff, a cosmetic surgical method is described. The method comprises successively orienting an ultrasound transmitter to transmit ultrasound from multiple locations adjacent the skin surface and at each of the multiple locations transmitting ultrasound, generating a time base, receiving ultrasound echoes, and determining from the time between transmission and reception the depth beneath the skin of tissue to be treated. The depths of the tissue at the multiple locations are stored in a memory associated with a programmable machine. The laser is successively targeted on each of the multiple locations, and at each of the multiple locations the depth of the tissue to be treated beneath that location is retrieved from the memory. The retrieved depth of the tissue to be treated beneath that location determines a laser excitation power that will achieve treatment of the tissue at the retrieved depth. The laser is excited at the determined excitation power.

As can be seen, the previously disclosed applications are limited to utilizing the ultrasonic image as a reference for laser ablation and/or coagulation. The application of ultrasonic imaging technique for the non-invasive phototherapy procedure is still a new territory to explore, where a two-dimensional (2-D) or a three-dimensional (3-D) ultrasonic image of the target tissue with much higher spatial resolution is required.

SUMMARY OF THE INVENTION

A phototherapy apparatus having a high-resolution ultrasonic imaging module is provided. The ultrasonic imaging module provides a two-dimensional (2-D) or a three-dimensional (3-D) image of a biological tissue from its surface layer to a depth of a few centimeters. The image is utilized to assess the condition of the biological tissue in order to optimize a phototherapy procedure in regard to: light intensity, wavelength, spot size, time duration, etc. as well as to evaluate the effectiveness of the phototherapy procedure.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
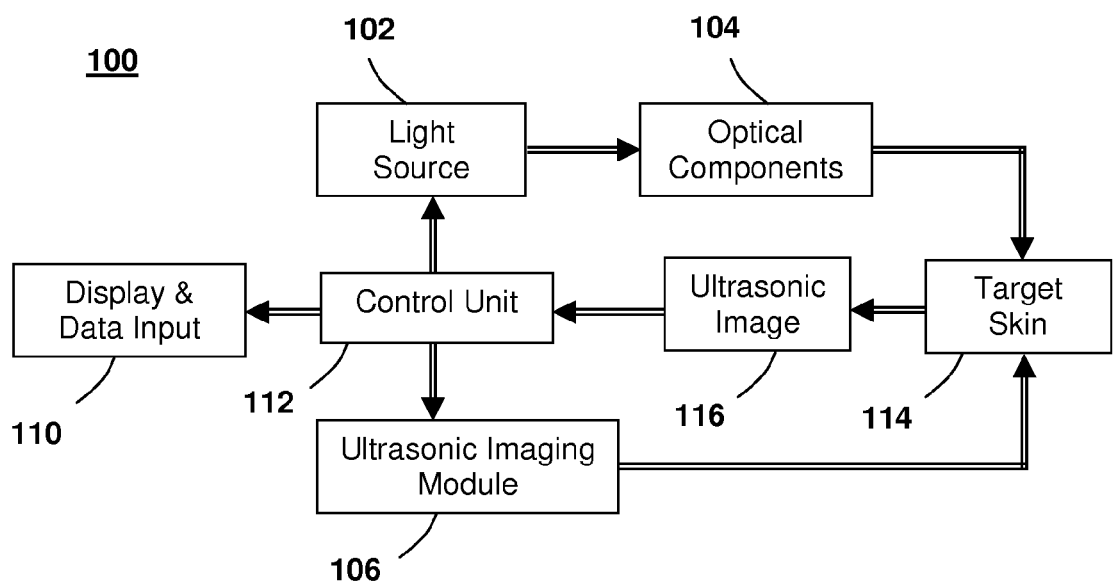
FIG. 1 shows the block diagram of an exemplary phototherapy apparatus for the treatment of pressure ulcer. The phototherapy apparatus comprises a built-in ultrasonic imaging module for diagnosing the condition of the target skin and evaluating the effectiveness of the phototherapy procedure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a phototherapy apparatus with built-in ultrasonic imaging module. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

In one preferred embodiment of the present invention, a phototherapy apparatus with a built-in ultrasonic imaging module is employed for diagnosis and treatment of pressure ulcer. Pressure ulcer or bedsore is a kind of ulcer caused by prolonged pressure or rubbing on vulnerable areas of the body. In its early stage, pressure ulcer appears in the subcutaneous tissue between the skin and bone as pockets of edema. Such dermal damage is hardly observable from the surface of the skin. But it can be identified by high resolution ultrasonic imaging, where the edema pockets appear as regions of low ultrasonic reflection. Referring a block diagram shown in FIG. 1, the phototherapy apparatus 100 comprises a light source 102 for treatment of the target skin 114, one or more optical components 104 for light delivery and beam control, an ultrasonic imaging module 106 to obtain an ultrasonic image 116 of the target skin 114, a common control unit 112 for data collection and controlling the light source 102, the ultrasonic imaging module 106, as well as other components of the phototherapy apparatus 100, and a display unit 110 as an user interface for data input and displaying the ultrasonic image 116 and the settings of the light source 102. The light source 102 can be an array of lasers, LEDs, or a filtered lamp that produce infrared and red light such as taught by Schubert V. in Photodermatology, Photoimmunology & Photomedicine, Vol. 17, No. 1, 2001, pp. 32-38, which is hereby incorporated herein by reference. The light produced by the light source 102 is delivered to the target skin through the optical components 104, which may comprise a group of lenses and one or more light guides, such as fiber bundles or liquid light guides. The light source can either operate in CW (continuous wave) mode or in pulsed mode through direct modulation or external modulation with an optical shutter.

Figure 2:
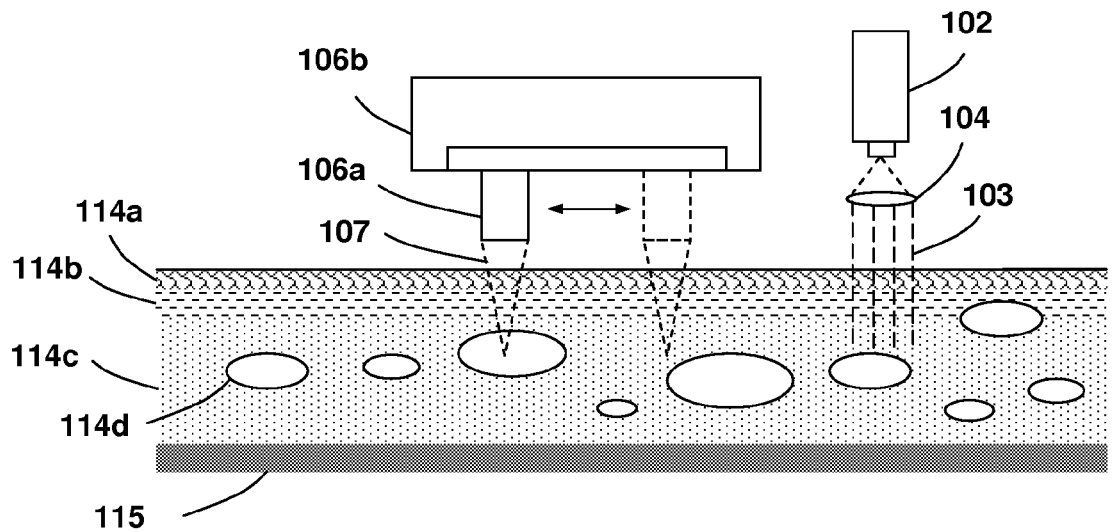
FIG. 2 illustrates the operation of the phototherapy apparatus shown in FIG. 1.

Referring further to FIG. 2, the ultrasonic imaging module 106 comprises a high frequency ultrasonic transducer 106a made of ceramic or polymer materials. The frequency of the produced ultrasound 107 is in the range of about several MHz to greater than 100 MHz. In order to have enough resolution for the intended application, typically the ultrasound frequency should be greater than 20 MHz in comparison with a few MHz used in standard or commonly known diagnostic ultrasonic scanners. The sound wave (or acoustic wave) 107 is focused to a spot having the size of several tens of microns and delivered to the skin through water or other sound conductive media (not shown). Depending on its frequency, the penetration depth of the acoustic wave into the skin is in the range of one to a few tens of millimeters. The structural information of the target skin 114 is inferred from the strength and phase of the echo, which is induced by acoustic impedance mismatch between different skin layers, e.g. the epidermis layer 114a, the dermis layer 114b, the subcutaneous layer 114c, and the bone 115 beneath the skin 114. In its early stage, pressure ulcer appears in the subcutaneous layer 114c as pockets of edema 114d, which can be identified from the ultrasonic image due to their low acoustic reflection. In a later stage of pressure ulcer, the pockets of edema may appear in the dermis layer 114b as well. In FIG. 2, the ultrasonic transducer 106a is mounted on a micro-motor 106b to scan across the target skin 114 in one lateral direction and obtain a two-dimensional (one lateral and one depth) image of the skin 114. The lateral resolution of the scan is limited by the spot size of the focused acoustic wave, while the depth resolution is determined by the wavelength of the acoustic wave, which is in the range of 15-75 µm depending on acoustic frequency. By incorporating lateral scan in the other direction, a three-dimensional (two lateral and one depth) image of the target skin can be acquired. The information obtained from the ultrasonic image, such as skin thickness, average skin density, location of the pockets of skin damage, provides an estimation of the skin condition. The skin condition is then used to optimize the parameters, e.g. light intensity, wavelength, spot size, duration time, repetition rate, duty cycle of the light source 102. For example, the duration time and intensity of the light source may be adjusted according to the skin thickness. The spot size of the light may be adjusted according to the size the edema pocket. During the phototherapy procedure, the therapeutic light beam 103 produced by the light source 102 is collimated by a lens 104 and penetrates into the target skin 114. The light beam 103 causes an increase of ATPase and activation of enzymes, which in turn induces an increase in the number of mast cells and the procollagen synthesis in fibroblasts to heal the pressure ulcer. The change of skin condition after the phototherapy procedure can be utilized to evaluate its effectiveness.

In similar manners, the disclosed phototherapy apparatus can be applied for treatment of other biological tissues where the employed light sources may differ in wavelength, light intensity, operation mode (continuous wave or pulsed), etc.

Figure 3:
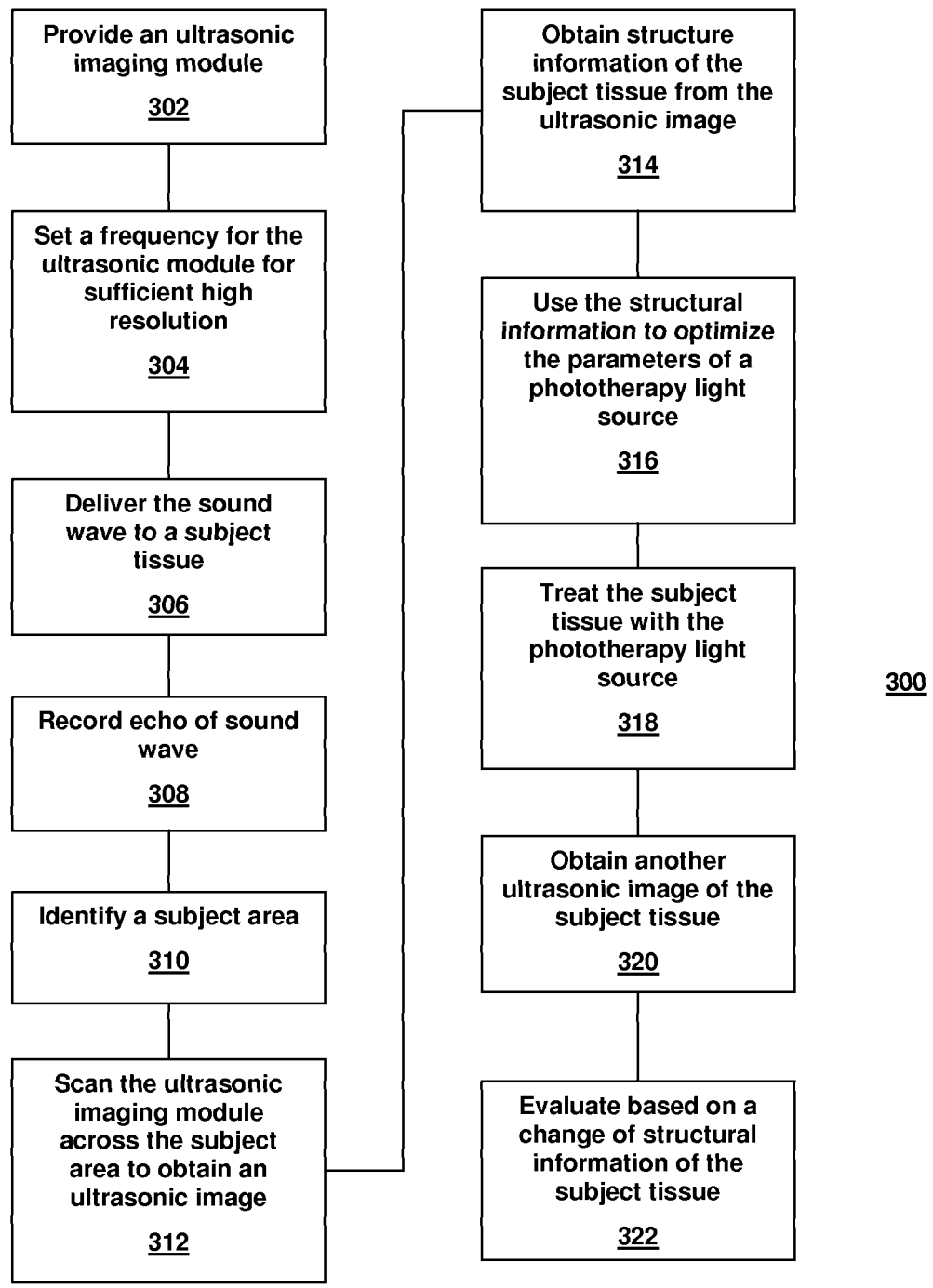
FIG. 3 shows a flowchart of using ultrasonic imaging technique as an aid for optimizing and evaluating phototherapy procedure.

Referring specifically to FIG. 3, a flowchart 300 depicting a method of making or using the present invention is provided. The method comprises the steps of: providing an ultrasonic imaging module (step 302); setting a frequency for the ultrasonic module for sufficient high resolution. Typically the ultrasound frequency should be greater than 20 MHz in comparison with a few MHz used in standard or commonly known diagnostic ultrasonic scanners (step 304); delivering the sound wave to a subject tissue (step 306); recording echo of sound wave from the subject tissue (step 308); identifying a subject area on the tissue to be treated (step 310); scanning the ultrasonic imaging module across the subject area to obtain an ultrasonic image (step 312); obtaining structural information of the subject tissue from the ultrasonic image, such as tissue thickness, average tissue density, and location of abnormal tissue (step 314); using the structural information to optimize the parameters of a phototherapy light source, such as light intensity, wavelength, spot size, duration time, repetition rate, and duty cycle (step 316); treating the subject tissue with the optimized phototherapy light source (step 318); obtaining another ultrasonic image of the subject tissue after treatment (step 320); and evaluating the treatment result based on a change of structural information of the subject tissue (step 322).

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for non-invasive treatment of skin tissue of human or animal targets, the method comprising the steps of:

providing at least one light source to produce light radiation in one or more wavelengths, wherein the light radiation is non-invasively applied or directed to the skin tissue to be absorbed thereof for sterilization, bio-stimulation, and/or photo-rejuvenation; and providing a high frequency ultrasonic imaging module, operatively coupled to the light source, to provide a high-resolution ultrasonic image revealing inner structural information of the skin tissue, wherein the inner structural information of the skin tissue is utilized to control and optimize a plurality of parameters of the light source and to evaluate the effectiveness of the phototherapy procedure;

wherein the ultrasonic frequency of the high frequency ultrasonic imaging module ranges from about 20 MHz to about 100 MHz.

2. The method of claim 1, wherein the plurality of parameters of the light source comprise light intensity, wavelength, spot size, duration time, repetition rate, and duty cycle.

3. The method of claim 1, wherein the inner structural information of the skin tissue comprises skin thickness, average skin density, and location of any pockets with skin damage.

* * * * *